(12) United States Patent
Seo et al.

(10) Patent No.: US 8,168,237 B2
(45) Date of Patent: May 1, 2012

(54) MEDICINAL HERBAL EXTRACT HAVING ANTI-OBESITY EFFECT

(75) Inventors: Jong-Bae Seo, Seoul (KR); Sun-Mi Choi, Seongnam (KR); Eun-Jung Choi, Incheon (KR); Sang-Wook Park, Seoul (KR); Eun-Wook Choi, Seoul (KR); Dong-Seung Seen, Suwon (KR); Tae-Gyu Lee, Seoul (KR)

(73) Assignee: Newgex Inc., Seoul (KR)

( * ) Notice: Subject to any disclaimer, the term of this patent is extended or adjusted under 35 U.S.C. 154(b) by 381 days.

(21) Appl. No.: 12/095,007

(22) PCT Filed: May 8, 2008

(86) PCT No.: PCT/KR2008/002584
§ 371 (c)(1),
(2), (4) Date: May 27, 2008

(87) PCT Pub. No.: WO2008/150068
PCT Pub. Date: Dec. 11, 2008

(65) Prior Publication Data
US 2010/0151057 A1      Jun. 17, 2010

(30) Foreign Application Priority Data
Jun. 8, 2007   (KR) .......................... 10-2007-0056192

(51) Int. Cl.
*A61K 36/00*       (2006.01)
(52) U.S. Cl. ....................................... 424/725
(58) Field of Classification Search ........................ None
See application file for complete search history.

(56) References Cited

U.S. PATENT DOCUMENTS

| | | | | |
|---|---|---|---|---|
| 6,657,100 | B1 * | 12/2003 | Underhill et al. | 604/361 |
| 7,407,674 | B2 * | 8/2008 | Suetake et al. | 424/725 |
| 2005/0064049 | A1 * | 3/2005 | Mori et al. | 424/725 |
| 2007/0218108 | A1 * | 9/2007 | Suetake et al. | 424/439 |
| 2010/0285156 | A1 * | 11/2010 | Seo et al. | 424/725 |

FOREIGN PATENT DOCUMENTS

| | | | |
|---|---|---|---|
| CN | 1091901 | * | 9/1994 |
| CN | 1126038 | * | 7/1996 |
| CN | 1130075 | * | 9/1996 |
| CN | 1132596 | * | 10/1996 |
| CN | 1101563 | * | 4/1999 |
| CN | 1253770 | * | 5/2000 |
| CN | 1391815 | * | 1/2003 |
| CN | 1415227 | * | 5/2003 |
| CN | 1426686 | * | 7/2003 |
| CN | 1616072 A | | 5/2005 |
| JP | 62-265236 A | | 11/1987 |
| JP | 03-220129 A | | 9/1991 |
| JP | 2005-008572 A | | 1/2005 |
| KR | 2000010275 | * | 2/2000 |
| KR | 20000010275 A | | 2/2000 |
| KR | 20010003366 A | | 1/2001 |
| KR | 2006119047 | * | 11/2006 |

OTHER PUBLICATIONS

Zhu et al. Linchan Huaaxue Yu Gongye. 1995. vol. 15, No. 2, pp. 67-71, CAPLUS Abstract enclosed.*
Suvitayavat et al. J. Ethnopharmacol. 2004. vol. 94, pp. 331-338.*
Li et al. Yaoxue Xuebao. 2007. vol. 42, No. 7, pp. 747-749, CAPLUS Abstract enclosed.*
Chang et al. Antiviral Res. 1988. vol. 9, No. 3, pp. 163-175, DRUGU Abstract enclosed.*

* cited by examiner

*Primary Examiner* — Christopher R. Tate
(74) *Attorney, Agent, or Firm* — Rosenberg, Klein & Lee

(57) ABSTRACT

Disclosed is an anti-obesity active extract obtained from a medicinal plant. More specifically, the extract obtained from *lysimachiae* foenum-graeci herba (which is a medicinal plant traditionally used in the East) can be used as an active ingredient for a raw material, a functional food, cosmetic, a crude drug, etc. for an obesity preventing or therapeutic agent because the extract can suppress the adipocyte differentiation and decrease the body weight and body fat in an obese animal, thereby suppressing fat accumulation (that is, a factor for obesity).

8 Claims, 6 Drawing Sheets

MEDICINAL HERBAL EXTRACT HAVING ANTI-OBESITY EFFECT

TECHNICAL FIELD

The present invention relates to an obesity preventing or therapeutic agent including an extract of *lysimachiae* foenum-graeci herba as an active ingredient, and more particularly to a raw material, a functional food, cosmetic, and a crude drug for preventing/treating obesity, which include an extract for suppressing the accumulation of fat, that is, a cause of obesity, the extract suppressing adipocyte differentiation and decreasing the body weight and body fat of an obese animal.

BACKGROUND ART

Obesity is a disease caused by a metabolic error, in which excessive energy in a body is converted into fat and the fat is excessively accumulated in adipose tissue, thereby abnormally increasing body fat. A factor causing obesity is largely divided into a genetic factor and an environmental factor (such as, a meat-oriented dietary life, a reduction of quantity of motion, etc.). Besides, there are other factors such as a neuroendocrine factor, a drug factor, etc.

Obesity, which has been already defined as a disease in 1996 by WHO, is one of the most rapidly increasing chronic diseases these days all over the world, and is a main dangerous factor causing "adult diseases" such as diabetes, hyperlipidemia, atherosclerosis, a cardiovascular system disease, etc. As direct and indirect expenses according to a sudden increase of obesity population have been increased all over the world, markets related to obesity and adult diseases have rapidly grown, thereby resulting in rapidly increased tendency of the extent of loss.

A target for treating such obesity includes controls of appetite, fat metabolism, adipocyte differentiation, fat absorption, energy metabolism, etc., and research focusing on the controls has been actively carried out. At present, there are two drugs for treating obesity, of which long term use is approved by the U.S. FDA, including sibutramine (REDUCTIL) having an action mechanism of suppressing reabsorption of norepinephrine and serotonin, and orlistat (XENICAL) having an effect by suppressing lipase secreted from the pancreas and digestive system. Sibutramine was originally developed as an antidepressant, but at present is used as an obesity therapeutic agent due to its excellent anti-obesity effect. According to recently reported research results, the use of sibutramine for at least one year or more resulted in a reduction of body weight by more than 4.3 kg, or 4.5%, as compared to a placebo group. However, the use of sibutramine gives rise to side effects, such as an increase in blood pressure, insomnia, xerostomia, vertigo, etc., and also, sibutramine has a disadvantage in that it cannot be used for a patient having a cardiovascular disease such as hypertension. Orlistat reduces absorption of fat included in an ingested food by about 30% by suppressing an action of lipase secreted from the pancreas and digestive system. According to recently reported research results, administration of orlistat for one year resulted in a reduction of body weight by 2.7 kg, or 2.9%, as compared to a placebo group. However, the use of orlistat gives rise to side effects, such as diarrhea, fatty stool, fecal incontinence, etc., and in the case of people ingesting a small amount of fat (such as Koreans), unlike Westerners, the effect of the drug is not significant. Due to limitations of drugs up to now developed in order to treat obesity, it is inevitably required to develop a drug having a new action mechanism, which has a high anti-obesity effect and gives rise to reduced side effects.

In using natural drugs that have been used for traditional medicine, there is no need to be deeply concerned over the toxicity caused by a developed drug because the natural drugs have been used for ages, and also there is very high possibility of finding a new active ingredient based on the demonstrated efficacy of a drug.

Therefore, the inventors of the present invention have tried to find a drug for suppressing adipocyte differentiation in order to find a more efficient obesity treating/preventing method using a natural drug of high economical efficiency and reduced side effects, and as a result, have completed the present invention by demonstrating that an extract of *lysimachiae* foenum-graeci herba (which is a medicinal plant) has a high effect on obesity prevention/treatment.

DISCLOSURE OF THE INVENTION

Therefore, the present invention has been made in view of the above-mentioned problems, and the present invention provides a raw material, a functional food, cosmetic, a crude drug, etc. for an obesity preventing or therapeutic agent, in which a *lysimachiae* foenum-graeci herba extract having a significant effect on suppression of adipocyte differentiation and a decrease in body weight and body fat in an obese animal model is included as an active ingredient.

The present invention characteristically includes an extract obtained from *lysimachiae* foenum-graeci herba, the extract displaying low cytotoxicity and having effects on suppression of adipocyte differentiation and a decrease in body weight and body fat in an obese animal model.

In preparation of an extract of *lysimachiae* foenum-graeci herba in the present invention, the present invention provides a method of extracting an extract having effects, such as suppression of adipocyte differentiation, and a decrease in body weight and body fat, from the *lysimachiae* foenum-graeci herba, the method including the steps of:

(1) drying and grinding *lysimachiae* foenum-graeci herba;

(2) carrying out solvent extraction by adding an organic solvent in an amount of 5 to 50 times by weight of *lysimachiae* foenum-graeci herba obtained in step (1); and (3) filtering extract solution of the organic solvent by using a filter paper, and carrying out vacuum concentration at temperature of 40□ or less.

A *lysimachiae* foenum-graeci herba extract of the present invention, which is obtained by the above method, has a very desirable effect on suppression of adipocyte differentiation and a decrease in body weight and body fat in an obese animal model, and thus can be used for a raw material, a functional food, cosmetic, a crude drug, etc. for an obesity preventing or therapeutic agent.

In an embodiment of the present invention, while NIH 3T3-L1 cells (that is, a preadipocyte cell line) are differentiated into adipocyte cells, an effect on suppression of adipocyte differentiation was inspected through treatment of the extract according to the present invention, and an effect on a decrease in body weight and body fat was observed by administering the extract to an obese animal model.

A composition according to the present invention includes the extract in an amount ranging from 0.1 to 50 wt %, based on a total weight of the composition. The composition including the *lysimachiae* foenum-graeci herba extract of the present invention may additionally appropriately include a carrier, an excipient, or a diluent according to a known method. Examples of the carrier, the excipient, or the diluent that may be included in the composition according to the present invention include lactose, dextrose, sucrose, sorbitol, mannitol, xylitol, erythritol, maltitol, starch, acacia senegal gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, mineral oil, etc. The composition including the extract according to the present invention may be prepared as any formulations, that is, oral forms (such as powder, granule, tablet, capsule, suspension, emulsion, syrup, aerosol, etc.), an external application form, a suppository, or a sterile injection solution according to a conventionally known method. Specifically, in formulation, diluent or excipient conventionally known in the art, such as filler, an extender, a binding agent, a wetting agent, a disintegrating agent, a surfactant, etc., may be used in preparation. A solid preparation for oral administration includes tablet, pill, powder, granule, capsule, etc., and such a solid preparation may be prepared by mixing the extract with at least one excipient (such as starch, calcium carbonate, sucrose, lactose, gelatin, etc.). Also, in addition to the excipient, lubricants, such as magnesium stearate, and talc, may be used. A liquid preparation for oral administration includes suspension, liquid for internal use, emulsion, syrup, etc., and in addition to a frequently used main diluent, such as water and liquid paraffin, the preparation may include a variety of excipients (for example, a wetting agent, a sweetening agent, an aromatic agent, a preservative, etc.). A formulation for parenteral administration includes a sterile aqueous solution, a nonaqueous solvent, suspension, emulsion, a freeze-dried preparation, and a suppository. As the nonaqueous solvent and the suspension, propylene glycol, polyethylene glycol, vegetable oil such as olive oil, injectable ester (such as ethyl oleate), etc. may be used. As a base for the suppository, witepsol, macrogol, tween 61, cacao butter, laurin butter, glycerogelatin, etc. may be used.

The dose of the extract according to the present invention may depend on the age, sex, and weight of a patient, but the extract may be administered in an amount of generally 0.01 to 500 mg/kg, and preferably 0.1 to 100 mg/kg once or several times a day. Also, the dose of the extract may be increased or decreased according to an administration route, severity of a disease, sex, weight, age, etc. Therefore, the present invention is not limited to the dose in any ways.

The composition according to the present invention may be administered to mammals such as a rat, a mouse, a domestic animal, a human, etc. through various routes. The administration of the composition may be carried out through all possible methods, for example, oral administration, rectal administration, intravenous injection, intramuscular injection, subcutaneous injection, intra-endometrial injection, intracerebroventricular injection. The *lysimachiae* foenum-graeci herba extract of the present invention has low toxicity and side effects, and thus may be used without anxiety during long-term administration for the purpose of prevention.

The present invention provides a health care food for preventing an anxiety disorder related to a cranial nerve system, which includes the *lysimachiae* foenum-graeci herba extract and a sitologically acceptable food supplement additive. The composition including the Chrysanthemum boreale extract of the present invention may be variously used for drugs, foods, drinks, etc. for preventing an anxiety disorder related to a cranial nerve system. The extract according to the present invention may be added to various foods, for example, drinks, gum, tea, a vitamin complex, health promoting foods, etc., and may be used in form of pills, powders, granules, infusion, tablets, capsules, or drinks. Herein, in the case of a health food composition according to the present invention, the extract may be generally added in an amount of 0.01 to 15 wt % based on the total weight of the food, and in the case of a health drink composition, the extract may be added in an amount of 0.02 to 10 g, preferably of 0.3 to 1 g, based on 100 ml.

The food supplement additive defined in the present specification includes food additives conventionally known in the art, for example, a fragrance agent, a flavouring agent, a coloring agent, filler, a stabilizer, etc. Besides the extract as an essential ingredient in a predetermined quantity, the health drink composition according to the present invention may include other ingredients without particular limitations, and may include various fragrance agents or natural starch, etc. as additives, in the same manner of conventional drinks. Examples of the natural starch include conventional sugar, such as monosaccharide (for example, glucose, fructose, etc.), disaccharide (for example, maltose, sucrose, etc.), polysaccharide (for example, dextrin, cyclodextrin, etc.), and sugar alcohol such as xylitol, sorbitol, erythritol, etc. Also, as the fragrance agent, a natural fragrance agent such as thaumatin, a stevia extract (for example, rebaudioside A, glycyrrhizin, etc.) and a synthetic fragrance agent such as saccharine, aspartame, etc. may be appropriately used. The natural starch is included in an amount of generally 1 to 20 g, and preferably about 5 to 12 g, based on 100 ml of the composition according to the present invention.

In addition, the composition according to the present invention may contain various nutrients, vitamins, minerals (electrolytes), a flavor agent (such as a synthetic flavor agent, a natural flavor agent, etc.), a coloring agent, an extender (cheese, chocolate, etc.), pectic acid and salt thereof, alginic acid and salt thereof, organic acid, a protective colloid thickener, a PH adjuster, a stabilizer, a preservative, glycerin, alcohol, a carbonating agent used for a carbonated drink, etc. Also, the composition according to the present invention may include flesh that may be used for preparing natural fruit juice, fruit juice drinks, and vegetable drinks. Each of such ingredients may be used independently or in any combination thereof. Although the percentages of such additives are not important, the additives are generally selected in the range of about 0 to 20 parts by weight, based on 100 parts by weight of the composition according to the present invention.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Reference will now be made in detail to the preferred embodiments of the present invention. However, the following examples are illustrative only, and the scope of the present invention is not limited thereto.

EXAMPLES

Example 1

Extraction of a *lysimachiae* foenum-graeci herba Extract

To dried and ground *lysimachiae* foenum-graeci herba, alcohol (methanol or ethanol) was added in an amount of 5 to 50 times by weight, and then reflux extraction was carried out for 24 hours or more to extract an active material. Then, an alcohol (methanol, ethanol, etc.) extract solution was filtered by using filter paper, and was subjected to vacuum concentration at a temperature of 40° C. or less.

Example 2

Measurement of Inhibitory Activity on Adipocyte Differentiation

Figure 1:
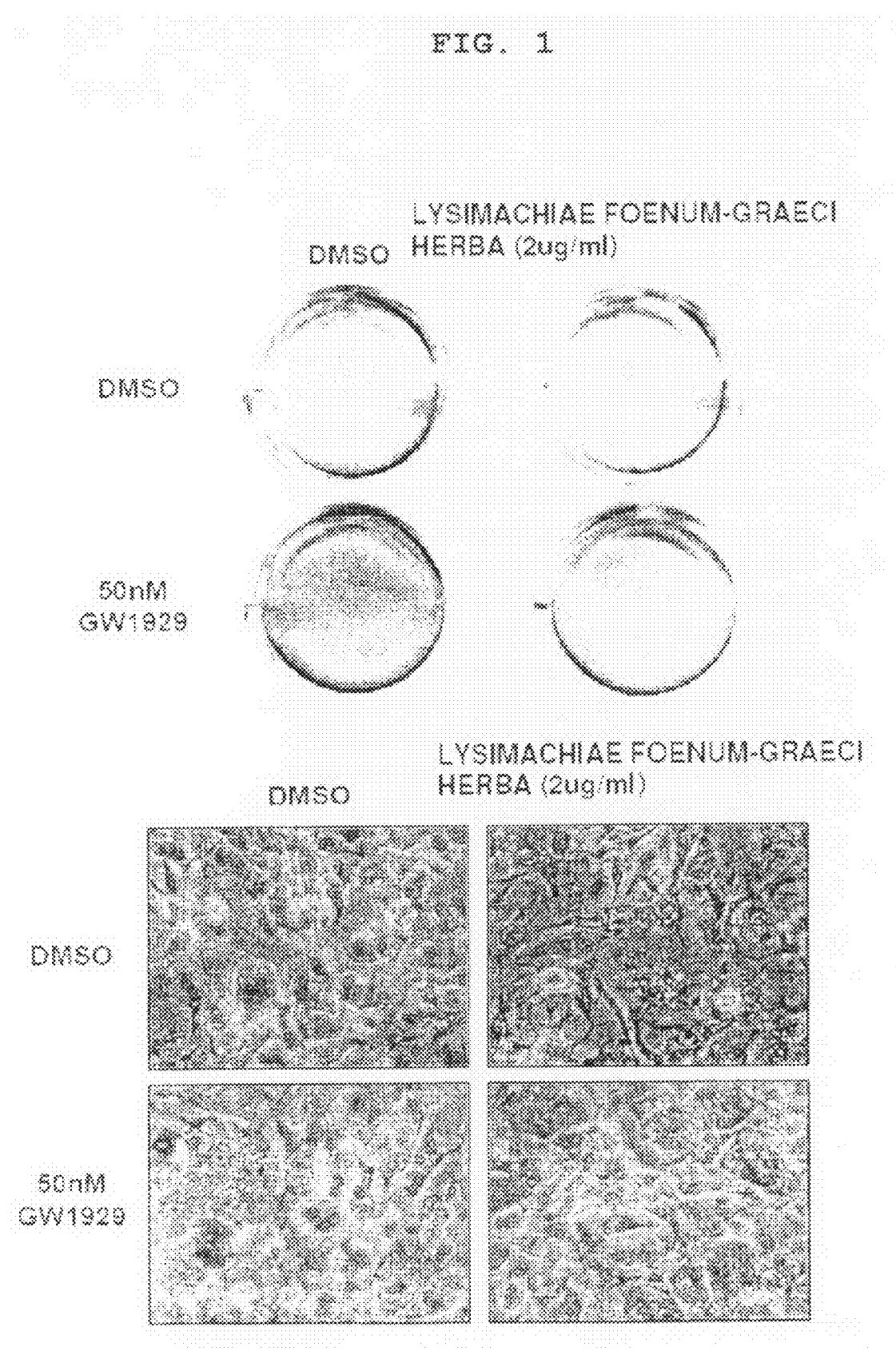
FIG. 1 illustrates photographs of preadipocyte cells and adipocyte cells which are observed through a microscope, after the preadipocyte cells and adipocyte cells are dyed with oil Red O.
Figure 2:
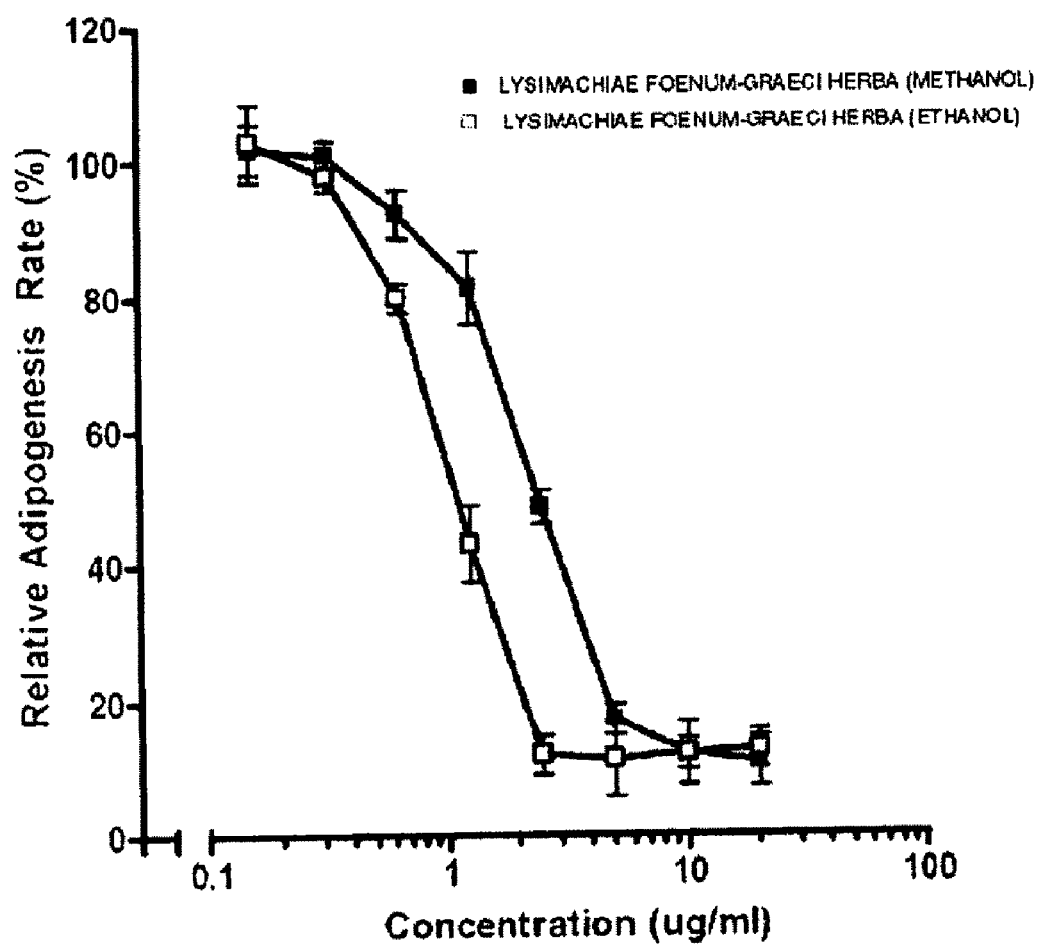
FIG. 2 is a graph illustrating suppression of adipocyte differentiation according to concentrations of a *lysimachiae* foenum-graeci herba extract.

NIH 3T3-L1 cells (ATCC CL173) (that is, a preadipocyte cell line) were cultured in a DMEM culture medium containing 10% BCS (bovine calf serum). When a cell density of preadipocytes became about 90% during the culture, Dexamethasone, IBMX (isobutylmethylxantine), and insulin were treated for about 48 hours. Then, adipocyte differentiation was induced by changing the culture medium into a medium containing insulin and 10% FBS (fetal bovine serum) every two days. The *lysimachiae* foenum-graeci herba extract obtained from Example 1 was treated with a concentration of 2 ug/ml from the initial induction step of adipocyte differentiation to compare the group treated with the *lysimachiae* foenum-graeci herba extract to a non-treated control group from the standpoint of inhibitory activity of adipocyte differentiation. Also, GW1929 (MERCK) (50 nM), which is an agonist of PPARgamma (peroxisome proliferator-activated receptor gamma, that is, a transcription factor of adipocyte differentiation), was treated to compare the treated group with a non-treated control group. The treatment was carried out until, in the control group, the adipocyte differentiation reached to 80% or more. Then, after dyeing with Oil Red O, adipocyte differentiation was observed through a microscope (see FIG. 1). Next, Nile Red (Sigma) for selectively dyeing neutral fat was used to detect neutral fat which was significantly accumulated during the adipocyte differentiation, and the inhibitory activity of the adipocyte differentiation was quantitatively measured. The *lysimachiae* foenum-graeci herba extract obtained from Example 1 was treated with concentrations ranging from 0.1 to 20 ug/ml from the initial induction step of adipocyte differentiation to compare the treated group to a control group. The treatment was carried out until in the control group, the adipocyte differentiation reached to 90% or more. Then, after dyeing with Nile Red, adipocyte differentiation was measured at 475 nm (see FIG. 2). In result, as shown in FIG. 1, it was determined that the *lysimachiae* foenum-graeci herba extract has a significant effect on the adipocyte differentiation. Also, when GW1929, that is, an agonist of PPARgamma, was treated, together with the *lysimachiae* foenum-graeci herba extract, it was determined that the adipocyte differentiation was suppressed, compared to a control group in which only GW1929 was treated so the adipocyte differentiation was facilitated. FIG. 2 illustrates suppression of adipocyte differentiation according to concentrations in alcohol extracts of *lysimachiae* foenum-graeci herba. The inhibitory activity (IC50) of the adipocyte differentiation by the *lysimachiae* foenum-graeci herba extract ranged from 1 to 3 ug/ml.

Example 3

Measurement of Cytotoxicity

Figure 3:
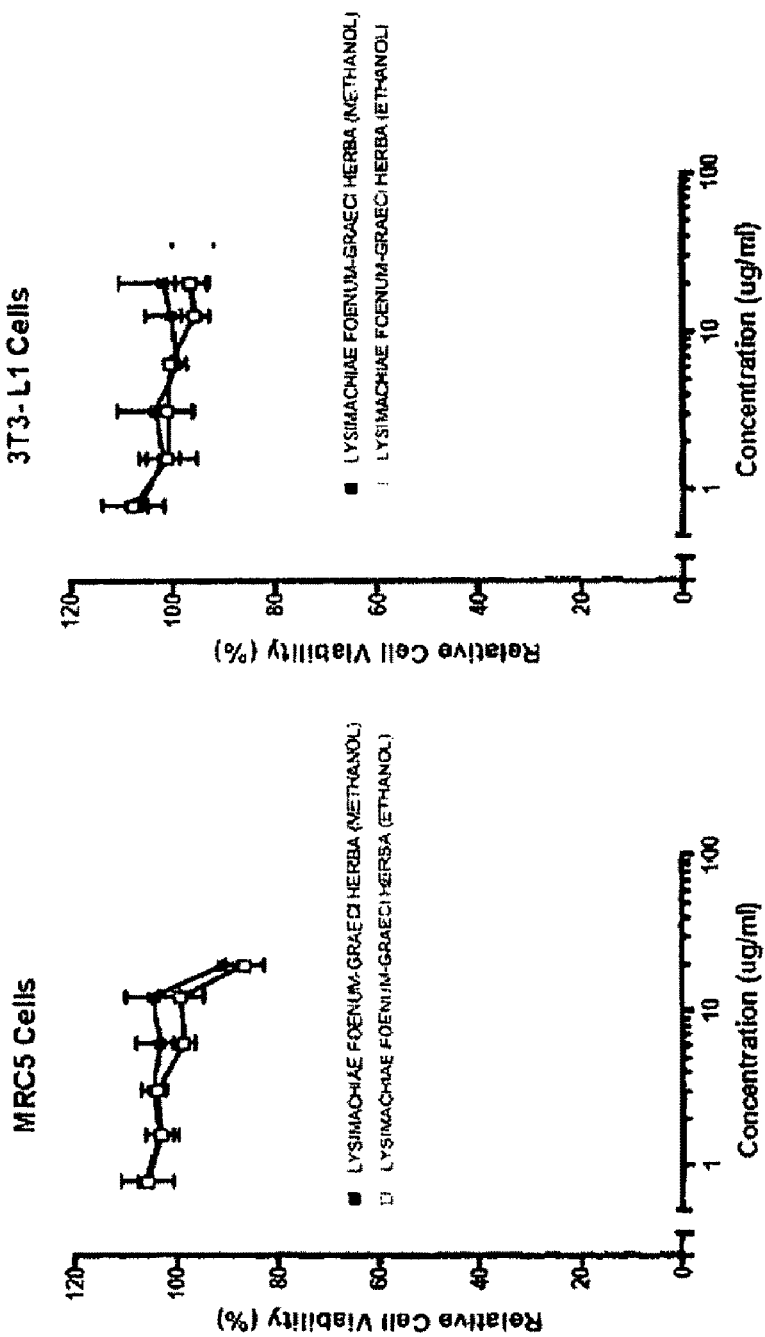
FIG. 3 shows graphs illustrating cytotoxicity according to concentrations of a *lysimachiae* foenum-graeci herba extract in cell lines of MRC5 and 3T3-L1.

MRC5 (ATCC) cells and NIH 3T3-L1 cells (ATCC CL173) were treated with the *lysimachiae* foenum-graeci herba extract obtained from Example 1 according to concentrations. Then, the number of live cells was measured to compare cytotoxicity of the treated group to cytotoxicity of a control group (see FIG. 3). As shown in FIG. 3, the cytotoxicity (CC50) of the *lysimachiae* foenum-graeci herba extract was more than 20 ug/ml.

Example 4

Figure 4:
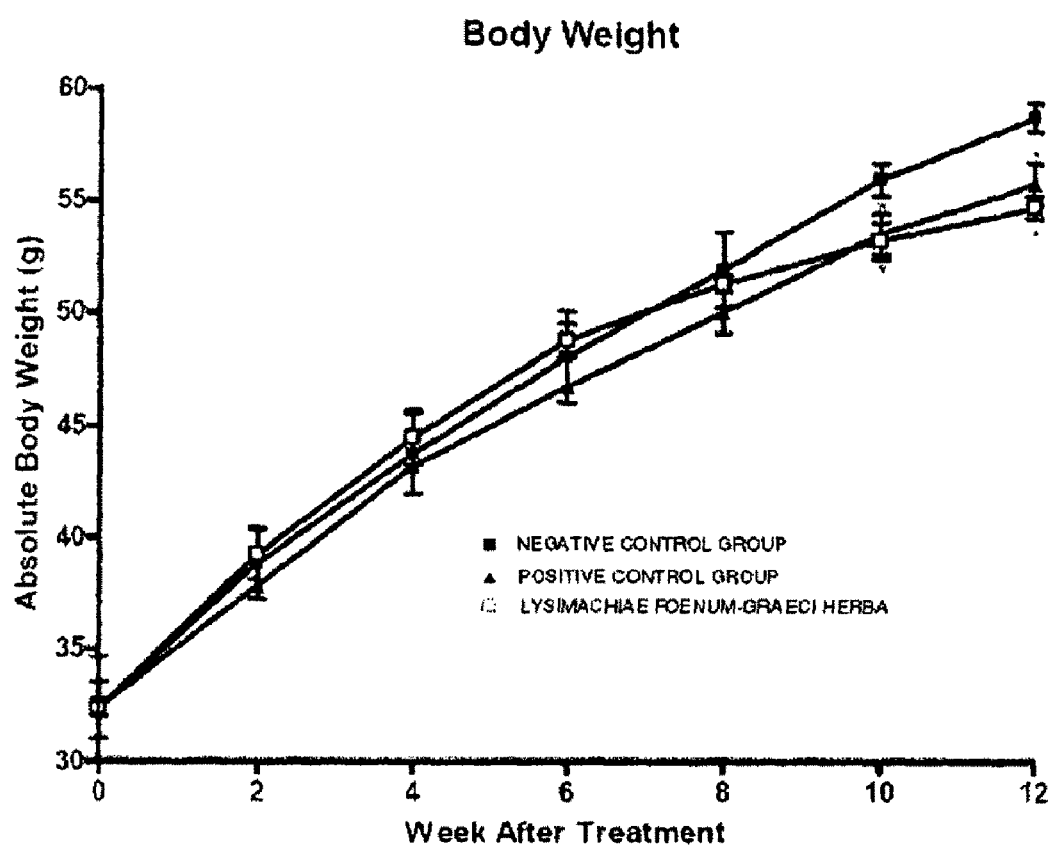
FIG. 4 is a graph illustrating a reducing effect on body weight after oral administration of a *lysimachiae* foenum-graeci herba extract to Lep ob/Lep ob mice (that is, an obese animal model)
Figure 5:
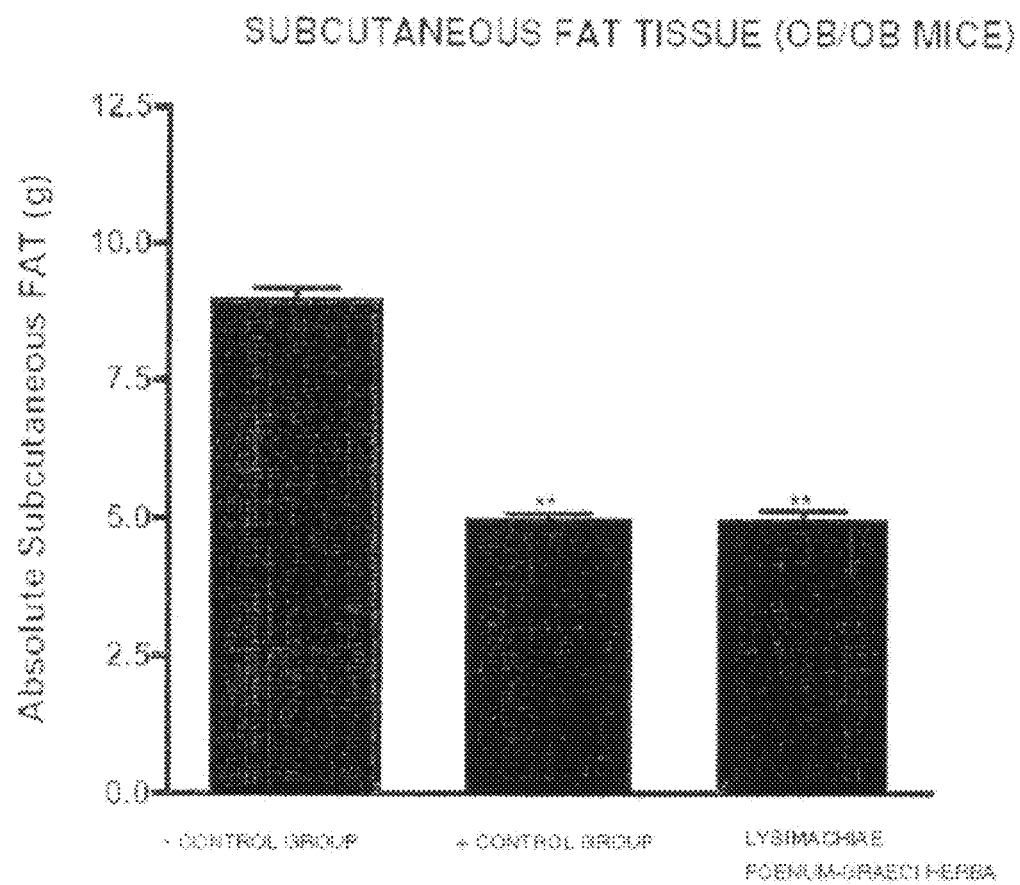
FIG. 5 shows graphs illustrating a reducing effect on body fat after oral administration of a *lysimachiae* foenum-graeci herba extract to Lep ob/Lep ob mice (that is, an obese animal model)
Figure 5:
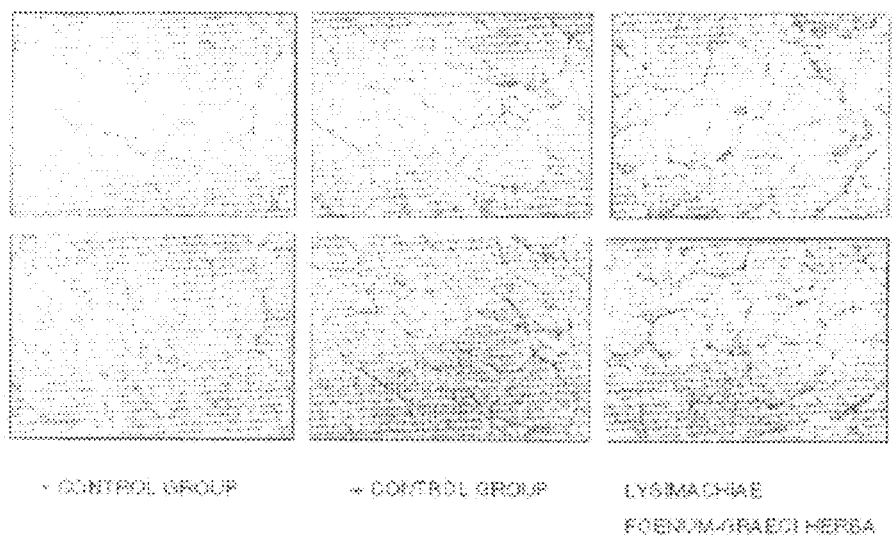

Inspection of the Effect of Obesity Prevention/Treatment in Lep ob/Lep ob Mice, That is, an Obese Animal Model C57BL/6JL Lep ob/Lep ob male mice (SPL, Japan) constantly ingest an excessive amount of food because the mice cannot control appetite due to secretion reduction of leptin by mutation of a leptin gene. In result, fat is excessively accumulated in the body, thereby increasing blood sugar, and thus, in about 10 to 11 weeks after birth, the body weight reaches about 50 g. Accordingly, in order to inspect of the obesity prevention/treatment effect, to each group including 5 Lep ob/Lep ob male mice (aged 7 weeks), the *lysimachiae* foenum-graeci herba extract obtained from Example 1 was orally administered with a concentration of 100 mg/kg/day for 12 weeks. Sibutramine (20 mg/kg/day) to a positive control group, and 0.5% methyl cellulose (MC) in the same amount to a negative control group, were administered. After the administration, internal organs were extracted to measure the weight thereof, and subcutaneous fat tissues were histologically analyzed (see FIGS. 4 and 5). Also, in the biochemical analysis of blood (such as a test on liver enzymes, AST/ALT) by blood-gathering of the mice, hepatotoxicity to the *lysimachiae* foenum-graeci herba extract was not shown. As shown in FIG. 4, the administration of the *lysimachiae* foenum-graeci herba extract resulted in significant reduction of body weight (P<0.05), similarly to the positive control group. FIG. 5 illustrates that the weight of subcutaneous fat tissues was significantly reduced by the administration of the *lysimachiae* foenum-graeci herba extract, similarly to a positive control group (P<0.001), and it is determined that the reason is the reduction of adipocyte size.

Example 5

Figure 6:
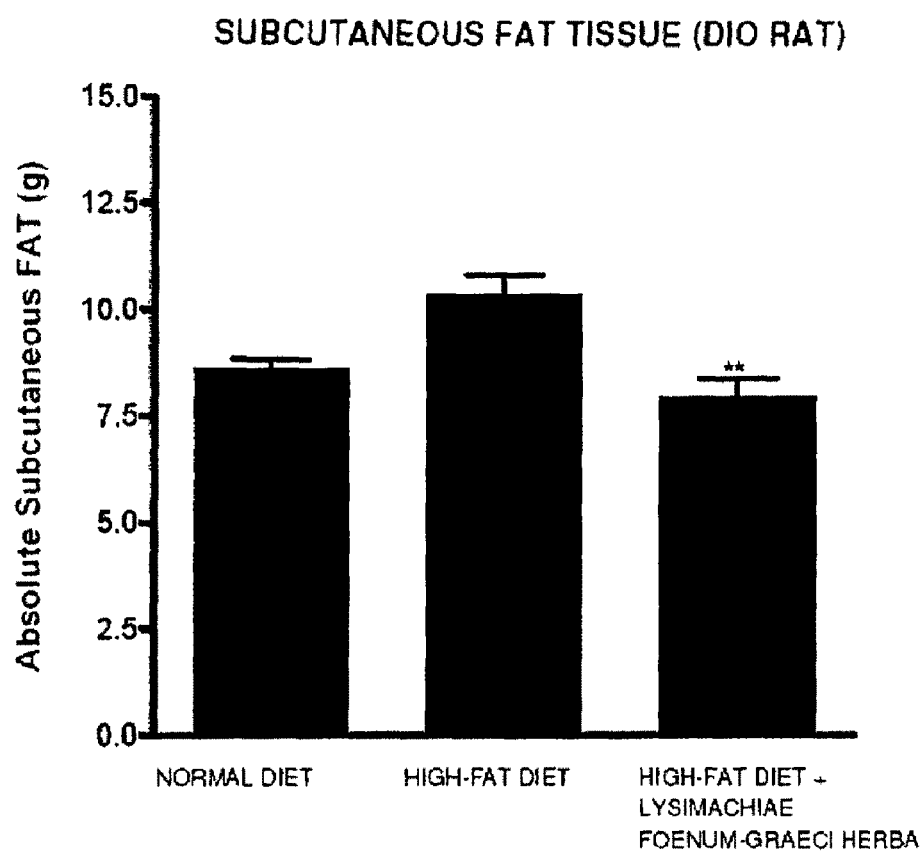
FIG. 6 is a graph illustrating a reducing effect on body fat after oral administration of a *lysimachiae* foenum-graeci herba extract to DIO (diet-induced obese) rats (that is, an obese animal model).

Inspection of the Effect of Obesity Prevention/Treatment in Diet-Induced Obese (DIO) Rats, That is, an Obese Animal Model In order to inspect of the obesity prevention/treatment effect, 3 groups, each of which including 8 SD (Sprague Dawley) male rats (DBL, Korea) (aged 8 weeks), were employed. To the groups, a normal diet, a high-fat diet, and a *lysimachiae* foenum-graeci herba extract together with a high-fat diet were orally administered, respectively, for 4 weeks (in an amount of 100 mg/kg/day for 2 weeks, and 50 mg/kg/day for 2 weeks). After the administration, internal organs were extracted to measure the weight thereof (see FIG. 6). Also, in the biochemical analysis of blood (such as a test on liver enzymes, AST/ALT) by blood-gathering of the rats, hepatotoxicity to the *lysimachiae* foenum-graeci herba extract was not shown. As shown in FIG. 6, it was determined that unlike a control group fed with a high-fat diet, subcutaneous fat was significantly reduced by the administration of the *lysimachiae* foenum-graeci herba extract, which is similar to a control group of a normal diet (P<0.05).

| Formulation Example 1 preparation of powder | |
|---|---|
| dried powder of *lysimachiae foenum-graeci* herba obtained from Exp. 1 | 300 mg |
| lactose | 100 mg |
| talc | 10 mg |

Powder is prepared by mixing the above ingredients and filling the ingredients into a sealing bag.

| Formulation Example 2 preparation of a tablet | |
|---|---|
| dried powder of *lysimachiae foenum-graeci* herba obtained from Exp. 1 | 50 mg |
| cornstarch | 100 mg |
| lactose | 100 mg |
| magnesium stearate | 2 mg |

A tablet is prepared by mixing the above ingredients and tabletting the ingredients according to a conventional method of preparing a tablet.

| Formulation Example 3 preparation of a capsule | |
|---|---|
| dried powder of *lysimachiae foenum-graeci* herba extract obtained from Exp. 1 | 50 mg |
| cornstarch | 100 mg |
| lactose | 100 mg |
| magnesium stearate | 2 mg |

A capsule is prepared by mixing the above ingredients and filling the ingredients into a gelatin capsule according to a conventional method of preparing a capsule.

| Formulation Example 4 preparation of injection | |
|---|---|
| dried powder of *lysimachiae foenum-graeci* herba obtained from Exp. 1 | 50 mg |
| Sterile water for injection | Proper quantity |
| pH adjuster | Proper quantity |

Injection is prepared by the above ingredients per ample (2 mg) according to a conventional method of preparing injection.

| Formulation Example 5 preparation of liquid formulation | |
|---|---|
| dried powder of *lysimachiae foenum-graeci* herba obtained from Exp. 1 | 100 mg |
| Isomerized sugar | 10 g |
| mannitol | 5 g |
| Purified water | Proper quantity |

A liquid formulation is prepared according to a conventional method of preparing liquid formulation, by the steps of: adding and dissolving each of the above ingredients in purified water; adding proper quantity of lemon fragrance; mixing the ingredients; adding purified water to the total mixture; regulating the mixture to 100 ml; and filling the mixture in a brown bottle and subjecting the mixture to sterilization.

| Formulation Example 6 preparation of a health food | |
|---|---|
| dried powder of *lysimachiae foenum-graeci* herba obtained from Exp. 1 | 1000 mg |
| vitamin mixture | proper quantity |
| vitamin A acetate | 70 μg |
| vitamin E | 1.0 mg |
| vitamin $B_1$ | 0.13 mg |
| vitamin $B_2$ | 0.15 mg |
| vitamin $B_6$ | 0.5 mg |
| vitamin $B_{12}$ | 0.2 μg |
| vitamin C | 10 mg |
| biotin | 10 μg |
| nicotinic acid amid | 1.7 mg |
| Folic acid | 50 μg |
| calcium pantothenate | 0.5 mg |
| inorganic mixture | proper quantity |
| ferrous sulfate | 1.75 mg |
| zinc oxide | 0.82 mg |
| magnesium carbonate | 25.3 mg |
| potassium dihydrogen phosphate | 15 mg |
| potassium monohydrogen phosphate | 55 mg |
| potassium citrate | 90 mg |
| calcium carbonate | 100 mg |
| magnesium chloride | 24.8 mg |

In the above composition including vitamins and minerals according to a preferred embodiment, although ingredients that are determined to be relatively appropriate for a health food are mixed, the mixing ratio may be changed. A health food composition may be prepared according to a conventional method of preparing a health food, the method including the steps of mixing the above ingredients, preparing granules, and using the granules in the composition in the same manner of a conventional method.

| Formulation Example 7 preparation of a health drink | |
|---|---|
| dried powder of *lysimachiae foenum-graeci* herba obtained from Exp. 1 | 1000 mg |
| citric acid | 1000 mg |
| oligosaccharide | 100 g |
| plum concentrate | 2 g |
| taurine | 1 g |
| purified water | 900 ml |

According to a conventional method of a health drink, the above ingredients are mixed and are agitation-heated for about 1 hour at 85° C.; the solution is filtered and is fed into a 2l sterilized container; and the solution is subjected to a sealing and sterilizing process and is kept refrigerated. Then, the final solution is used for preparing the health drink composition according to the present invention.

In the above composition according to a preferred embodiment, although ingredients that are determined to be relatively appropriate for a favorite drink are mixed, the mixing ratio may be changed according to regional/national preferences, such as classes, nations, purposes of consumers.

INDUSTRIAL APPLICABILITY

As can be seen from the foregoing, a *lysimachiae* foenum-graeci herba extract according to the present invention has a high anti obesity effect, such as effects on suppression of adipocyte differentiation and a decrease in body weight and body fat in an obese animal model, and thus may be used as an active ingredient for a raw material, a functional food, cosmetic, a crude drug, etc. for an obesity preventing or therapeutic agent.

While this invention has been described in connection with what is presently considered to be the most practical and exemplary embodiment, it is to be understood that the invention is not limited to the disclosed embodiment and the drawings, but, on the contrary, it is intended to cover various modifications and variations within the spirit and scope of the appended claims.

The invention claimed is:

1. A method for treating obesity in a subject in need thereof, comprising:
   (1) obtaining an extract from *lysimachiae* foenum-graeci herba by:
      (a) drying and grinding *lysimachiae* foenum-graeci herba;
      (b) carrying out solvent extraction by adding an alcoholic solvent in an amount based upon the weight of *lysimachie* foenum-graeci herba obtained in step (1)(a) to obtain an abstract solution; and
      (c) filtering the extract solution by using filter paper, and carrying out vacuum concentration at a specific temperature to obtain the *lysimachiae* foenum-graeci herba extract; and
   (2) administering a therapeutically effective amount of the *lysimachiae* foenum-graeci herba extract to the subject, wherein the subject is a human or a non-human animal.

2. The method as claimed in claim 1, wherein administering the extract has inhibitory activity of adipocyte differentiation in the subject.

3. The method as claimed in claim 1 or 2, wherein the extract is formulated in the form of a capsule, tablet, granule, powder, or drink.

4. The method as claimed in claim 1 or 2, wherein the extract is administered in an amount of 0.01 to 500 mg/kg/day.

5. The method as claimed in claim 1 or 2, wherein the extract is administered by oral administration, rectal administration, intravenous injection, intramuscular injection, subcutaneous injection, intra-endometrial injection or intracerebroventricular injection.

6. The method as claimed in claim 1 or 2, wherein the alcoholic solvent of step (1)(b) is added in an amount of 5 to 50 times by weight of the *lysimachiae* foenum-graeci herba obtained in step (1)(a).

7. The method as claimed in claim 1 or 2, wherein the vacuum concentration of step (1)(c) is carried out at a temperature of 40° C. or less.

8. The method as claimed in claim 1 or 2, wherein the alcoholic solvent comprises methanol or ethanol.

* * * * *